United States Patent
Clary-Ceccato et al.

(10) Patent No.: US 9,034,898 B2
(45) Date of Patent: May 19, 2015

(54) FGF RECEPTOR (FGFR) AGONIST DIMERIC COMPOUNDS, PROCESS FOR THE PREPARATION THEREOF AND THERAPEUTIC USE THEREOF

(71) Applicant: Sanofi, Paris (FR)

(72) Inventors: Marie-Line Clary-Ceccato, Paris (FR); Nathalie Guillo, Paris (FR)

( * ) Notice: Subject to any disclaimer, the term of this patent is extended or adjusted under 35 U.S.C. 154(b) by 0 days.

(21) Appl. No.: 14/369,160

(22) PCT Filed: Dec. 26, 2012

(86) PCT No.: PCT/IB2012/057727
§ 371 (c)(1),
(2) Date: Jun. 26, 2014

(87) PCT Pub. No.: WO2013/098764
PCT Pub. Date: Jul. 4, 2013

(65) Prior Publication Data
US 2015/0011579 A1    Jan. 8, 2015

(30) Foreign Application Priority Data

Dec. 28, 2011    (FR) ...................................... 11 62485

(51) Int. Cl.
| | | |
|---|---|---|
| C07D 401/14 | (2006.01) | |
| A61K 31/437 | (2006.01) | |
| A61K 31/4353 | (2006.01) | |
| C07D 471/04 | (2006.01) | |
| C07D 519/00 | (2006.01) | |

(52) U.S. Cl.
CPC ............ *C07D 471/04* (2013.01); *C07D 401/14* (2013.01); *A61K 31/437* (2013.01); *C07D 519/00* (2013.01)

(58) Field of Classification Search
CPC ............... C07D 401/14; A61K 31/437; A61K 31/314353
USPC ........................................... 514/303; 546/119
See application file for complete search history.

(56) References Cited

U.S. PATENT DOCUMENTS

2007/0161673 A1 *    7/2007    Barker et al. .................. 514/303

FOREIGN PATENT DOCUMENTS

| WO | WO2007080325 A1 | 7/2007 |
|---|---|---|
| WO | WO2011023081 A1 | 3/2011 |

OTHER PUBLICATIONS

Alavi, Alireza et al. (2003) Role of Raf in Vascular Protection from Distinct Apoptotic Stimuli, Science, vol. 301, pp. 94-96.
Andrade, Silvia et al.(1997) Sponge-Induced Angiogenesis in Mice and the Pharmacological Reactivity of the neovasculature Quantitated by a Fluorimetric Method, Microvascular Research 54, pp. 253-261.
Burger, Patricia et al. (2002) Fibroblast growth factor receptor-1 is expressed by endothelial progenitor cells, Blood, vol. 100, No. 10, pp. 3527-3535.
Ornitz et al. (2001) Review Fibroblast growth factors, Genome biology, vol. 2 No. 3, pp. 1-12.
Fibbi, G. et al (2002) Growth Factor-Dependent Proliferation and Invasion of Muscle Satellite Cells Require the Cell-Associated Fibrinolytic System, Biol. Chem, vol. 383, pp. 127-136, Walter de Gruyter, Berlin, N.Y.
Freedman, S.B. et al. (2001) Therapeutic Angiogenesis for Ischemic Cardiovascular Disease, J Mol Cell Cardiol, vol. 33, pp. 379-393.
Freedman, S.B. et al. (2002) Therapeutic Angiogenesis for Coronary Artery Disease, Ann. Intern. Med., vol. 136, pp. 54-71.
Hamacher, J. et al. (2002) Tumor Necrosis Factor-a and Angiostatin Are Mediators of Endothelial Cytotoxicity in Bronchoalveolar Lavages of patients with Acute Respiratory Distress Syndrome, American Journal of Respiratory and Critical Care Medicine, vol. 166, pp. 651-656.
Hendel, R. et al. (2000) Effect of Intracoronary Recombinant Human Vascular Endothelial Growth Factor on Myocardial Perfusion: Evidence for a Dose-Dependent Effect, Circulation, vol. 101, pp. 118-121.
Kawagushi, H. et al. (2001) Acceleration of Fracture Healing in Nonhuman Primates by Fibroblast Growth Factor-2, Journal of Clinical Endocrinology & Metabolism, vol. 86, No. 2, pp. 875-880.
Khurana, R. et al. (2003) Insights from Angiogenesis Trials Using Fibroblast Growth Factor for Advanced Arteriosclerotic Disease, Trends Cardiovasc Med, vol. 13, No. 3, pp. 116-122.

(Continued)

*Primary Examiner* — Niloofar Rahmani
(74) *Attorney, Agent, or Firm* — McDonnell Boehnen Hulbert & Berghoff LLP

(57) ABSTRACT

The invention relates to novel heterocyclic compounds which are pyrazolopyridine derivatives that induce fibroblast growth factor receptor (FGFR) dimerization, having the general formula: $M_1$-L-$M_2$ in which $M_1$ or $M_2$, which may be identical or different, each represent, independently of one another, a monomer unit M and L represents a linker group which links $M_1$ and $M_2$ covalently with the monomer unit which follows: Process for the preparation thereof and therapeutic use thereof.

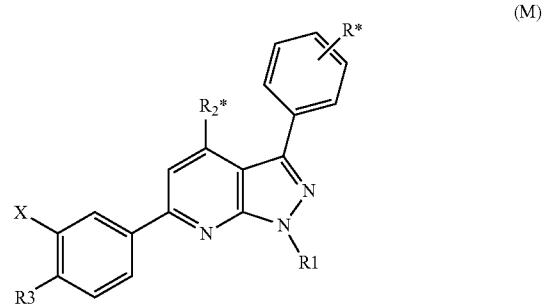

13 Claims, No Drawings

(56) References Cited

OTHER PUBLICATIONS

Klimaschewski, L. et al. (2004) Basic Fibroblast Growth Factor Isoforms Promote Axonal Elongation and Branching of Adult Sensory Neurons In Vitro, Neuroscience 126, pp. 347-353.

Koide, K. et al. (2001) A Synthetic Library of Cell-Permeable Molecules, Am. Chem. Soc., vol. 123, pp. 398-408.

Latham, RJ et al. (1999) Local Perivascular Delivery of Basic Fibroblast Growth Factor in Patients Undergoing Coronary Bypass Surgery: Results of a Phase I Randomized, Double-Blind, Placebo-Controlled Trial, Circulation, vol. 100, pp. 1865-1871, American Heart Association.

Latham, RJ et al. (2000) Intracoronary Basic Fibroblast Growth Factor (FGF-2) in Patients With Severe Ischemic Heart Disease: Results of a Phase I Open-Label Dose Escalation Study, Journal of the American College of Cardiology, vol. 36, No. 7, pp. 2132-0.

Lazarous, D. et al. (2000) Basic Fibroblast Growth Factor in Patients With Intermittent Claudication: Results of a Phase I Trial, Journal of the Am College of Cardiology, vol. 36, No. 4, pp. 1239-1244.

Neuhaus, P. et al. (2003) Reduced Mobility of Fibroblast Growth Factor (FGF)-Deficient Myoblasts Might Contribute to Dystrophic Changes in the Musculature of FGF2/FGF6/mdx Triple-Mutant Mice, Mol. Cell. Biol., vol. 23 (17), pp. 6037-6048.

Qureshi, S. et al. (1999) Mimicry of erythropoietin by a nonpeptide molecule, PNAS, vol. 96, No. 21, pp. 12156-12161.

Rydh-Rinder, M et al. (2001) Glutamate release from adult primary sensory neurons in culture is modulated by growth factors, Regulatory Peptides, vol. 102, pp. 69-79.

Sakurai, T et al. (2004) The efficient provascularization induced by fibroblast growth factor 2 with a collagen-coated device improves the cell survival of a bioartificial pancreas, Pancreas, vol. 28, No. 3, pp. e70-e79.

Seed, Brian (1994) Making agonists of antagonists, Chemistry & Biology, vol. 1, pp. 125-129.

Sherer, D et al. (2000) Antiogenesis during implantation, and placental and early embryonic development, Placenta, vol. 22, pp. 1-13.

Simons, M. et al. (2002) Pharmacological treatment of coronary artery disease with recombinant fibroblast growth factor-2: double-blind, randomized, controlled clinical trial, Circulation, vol. 105, pp. 788-793, American heart association.

Unger, E. et al. (2000) Effects of a single intracoronary injection of basic fibroblast growth factor in stable angina pectoris, Am J Cardiol, vol. 85, pp. 1414-1419.

Welm, BE (2002) Inducible dimerization of FGFR1: development of a mouse model to analyze progressive transformation of the mammary gland, The Journal of Cell Biology, vol. 157, No. 4, pp. 703-714.

Zare, Leila (2011) Convenient ultrasound-promoted regioselective synthesis of fused 6-amino-3-methyl-4-aryl-1H-pyrazolo[3,4-b]pyridine-5-carbonitrile, Synthetic Communications, vol. 41, pp. 2323-2330.

* cited by examiner

FGF RECEPTOR (FGFR) AGONIST DIMERIC COMPOUNDS, PROCESS FOR THE PREPARATION THEREOF AND THERAPEUTIC USE THEREOF

This application is a national stage application under 35 U.S.C. §371 of International Application No. PCT/IB2012/057727, filed Dec. 26, 2012, which claims priority to French Patent Application No. 1162485, filed Dec. 28, 2011, the disclosure of which are explicitly incorporated by reference herein.

The subject of the present invention is novel heterocyclic compounds which are pyrazolopyridine derivatives that induce Fibroblast Growth Factor Receptor (FGFR) dimerization, to the process for the preparation thereof and to the therapeutic uses thereof. The subject of the present invention is in particular novel compounds with a dimeric structure, as FGFR agonists.

FGFs are a family of polypeptides synthesized by a large number of cells during embryonic development and by cells of adult tissues under various pathological conditions.

FGF2 (or b-FGF) is the first and the most well-characterized of these growth factors. FGF2 is an 18 kDalton (kDa) protein which induces proliferation, migration and protease production by numerous cells, and in particular endothelial cells, fibroblasts, smooth muscle cells or alternatively bone cells. FGF2 interacts with the cells by means of two classes of receptors, high-affinity receptor tyrosine kinases (FGFRs) and low-affinity heparan sulphate proteoglycan (HSPG) type receptors located at the cell surface and in extracellular matrices. Thus, FGF2 and its receptors represent very relevant targets for therapies aimed at activating processes of angiogenesis, and of regeneration of smooth muscle cells, bone cells and hair-follicle cells.

Moreover, it is known that cell surface receptor tyrosine kinases transmit information through the plasma membrane in particular via mechanisms of dimerization of the extracellular domains of these receptors.

Known ligands capable of activating these dimerization mechanisms are typically natural compounds, such as FGFs, PDGF (Platelet-Derived Growth Factor), VEGF (Vascular Endothelial Growth Factor), EPO (Erythropoietin), G-CSF (Granulocyte-Colony Stimulating Factor), TPO (Thrombopoietin), certain cytokines or insulin.

B. Seed (*Chemistry and Biology*, November, 1994, 1, 125-129) puts forward the general principle that it would be possible to construct agonists of these receptors by dimerization of antagonists. However, there is no described example of a synthetic molecule constructed according to this concept. Articles such as S A. Qureshi (PNAS, 1999, vol 96, no 21, 12156-12161), B E. Welm (The Journal of cell biology, 2002, vol 157, 4, 703-714), K. Koide (J. Am. Chem. Soc., 2001, 123, 398-408) describe non-peptide compounds or chemical inducers of dimerization (CID), these compounds acting on chimeric receptors and not on natural receptors. They do not present any results showing that a CID makes it possible to activate the signalling pathway of a natural receptor.

In vertebrates, there are 22 members in the family of FGFs with a molecular weight ranging from 17 to 34 kDa and which share between 13% and 71% homology. These FGFs are highly conserved both at the gene level and at the amino acid sequence level. (D Ornitz. & N. Itoh, Fibroblast growth factors. Genome Biology, 30005.1-3005.12, 2001). FGFs interact with cells by means of high-affinity receptor tyrosine kinases (FGF-R1, -R2, -R3, -R4). The expression of FGFs suggests that they have an important role in development. Among the FGF family, FGF-2 is the FGF which has been most widely described. It is an 18 kDa protein which induces proliferation, migration and protease production on various cell types, such as endothelial cells, smooth muscle cells, fibroblasts, pericytes, osteoblasts or hair-follicle cells. Thus the main therapeutic areas in which FGF2 is involved include neuronal and cardiovascular physiology, nerve regeneration, nociception, tissue repair, homoeostasis, and bone repair.

Thus, FGF2 and its receptors represent very relevant targets for therapies aimed at inducing angiogenesis and arteriogenesis processes (Khurana, R. & Simons, M. Insights from angiogenesis trials using fibroblast growth factor for advanced arteriosclerotic disease. Trends Cardiovasc Med 13, 116-22, 2003). When a blood vessel is obstructed, an ischaemic phase is observed, which induces a decrease in arterial circulation in an organ, thereby leading to a decrease in oxygen concentration in the damaged tissues. It has been shown in vitro and in vivo that several growth factors stimulate angiogenesis and arteriogenesis processes. FGF2 also induces neovascularization in vivo and also the development of collateral vessels after ligature of a vessel in pharmacological models.

Several pieces of evidence demonstrate that FGF2 is also involved in the differentiation of angioblasts into endothelial progenitor cells and thus participates in revascularization following occlusion (Burger, P. E. et al. Fibroblast growth factor receptor-1 is expressed by endothelial progenitor cells. Blood 100, 3527-35, 2002). Thus, strategies aimed at increasing the response of the cells of the vascular tree are suitable strategies for increasing post-ischaemic and in particular cardiac or coronary-artery revascularization (Freedman, S. B. & Isner, J. M. Therapeutic angiogenesis for ischemic cardiovascular disease. J Mol Cell Cardiol 33, 379-93, 2001; Freedman, S. B. & Isner, J. M. Therapeutic angiogenesis for coronary artery disease. Ann Intern Med 136, 54-71, 2002).

As regards the treatment of cardiac ischaemia, one of the most promising clinical trials is a trial in which FGF2 was sequestered in alginate microspheres in the presence of heparin (Laham, R. J. et al. Local perivascular delivery of basic fibroblast growth factor in patients undergoing coronary bypass surgery: results of a phase I randomized, double-blind, placebo-controlled trial. Circulation 100, 1865-71, 1999). After 90 days, all the patients treated with FGF2 showed no ischaemic cardiac symptom. In comparison, in the control group, 3 of the 7 patients had persistent symptoms at 90 days, and 2 patients had recourse to vascular surgery. Interestingly, the benefit of the therapy was maintained after 3 years of follow-up. Furthermore, three clinical trials on the injection of FGF2 into the coronary artery were carried out in the treatment of narrowing of the coronary arteries (Laham, R. J. et al. Intracoronary basic fibroblast growth factor (FGF-2) in patients with severe ischemic heart disease: results of a phase I open-label dose escalation study. J Am Coll Cardiol 36, 2132-9, 2000; Simons, M. et al. Pharmacological treatment of coronary artery disease with recombinant fibroblast growth factor-2: double-blind, randomized, controlled clinical trial. Circulation 105, 788-93, 2002; Unger, E. F. et al. Effects of a single intracoronary injection of basic fibroblast growth factor in stable angina pectoris. Am J Cardiol 85, 1414-9, 2000). The result of these three trials shows that intra-coronary infusions of FGF2 are well tolerated and significantly improve the clinical condition of the patients.

In another phase-I clinical trial, patients with peripheral artery disease leading to claudication received FGF2 injections (Lazarous, D. F. et al. Basic fibroblast growth factor in patients with intermittent claudication: results of a phase I trial. J Am Coll Cardiol 36, 1239-44, 2000). In this context, FGF2 was well tolerated in these patients and the clinical data suggest a beneficial effect of FGF2 in particular on improvement of walking in patients with peripheral disease, for instance Buerger's disease or thromboangiitis obliterans, which affects the distal vascular structures and which is characterized by distal arteritis in the legs, accompanied by pain and ulceration.

In another context requiring improved angiogenesis it has just been clearly demonstrated, in diabetic rats, that vascularization in bioartificial pancreases was much greater when the pancreases were impregnated with microspheres carrying FGF2 (Sakurai, Tomonori; Satake, Akira, Sumi, Shoichiro, Inoue, Kazutomo, Nagata, Natsuki, Tabata, Yasuhiko. The Efficient Prevascularization Induced by Fibroblast Growth Factor 2 With a Collagen-Coated Device Improves the Cell Survival of a Bioartificial Pancreas. Pancreas. 28(3):e70-e79, April 2004). This revascularization thus improves the survival of the implanted bioartificial pancreases and, consequently, the survival of the graft. Thus, FGFs appear to contribute to improving bioartificial pancreatic graft survival in the diabetic patient and, more generally, appear to contribute to improving graft revascularization and appear to be involved in graft survival.

In addition to the angiogenesis-inducing effects, FGF2 protects endothelial cells against inducers of apoptosis. It has now been clearly described that FGF2 is an endothelial cell survival factor (Role of Raf in Vascular Protection from Distinct Apoptotic Stimuli: A Alavi, J. D. Hood, R. Frausto, D. G. Stupack, D. A. Cheresh: Science 4 Jul. 2003: Vol. 301. no. 5629, pp. 94-96). Acute respiratory distress syndrome (ARDS) is characterized by cardiovascular and neuropsychiatric problems. In the context of the cardiovascular problems, patients exhibit considerable vascular damage and in particular a high level of induction of endothelial cell apoptosis. Recently, Hamacher et al. have demonstrated that bronchoalveolar lavage fluids from patients suffering from ARDS exhibit pro-apoptotic activity against lung microvascular endothelial cells (Tumor necrosis factor-alpha and angiostatin are mediators of endothelial cytotoxicity in bronchoalveolar lavages of patients with acute respiratory distress syndrome. Am J Respir Crit. Care Med. 2002 Sep. 1; 166(5):651-6: Hamacher J, Lucas R, Lijnen H R, Buschke S, Dunant Y, Wendel A, Grau G E, Suter P M, Ricou B.).

Pre-eclampsia is a pathological condition of the placenta which is associated with a deficiency in vascularization (Sherer, D. M. & Abulafia, O. Angiogenesis during implantation, and placental and early embryonic development. Placenta 22, 1-13, 2001). These deficiencies in vascularization are thought to be due to a deficiency in angiogenesis and to lead to disruptions at the level of the placenta that can result in death of the foetus.

Healing is a tissue regeneration process which does not require treatment in most cases. However, complications can occur, such as infection or the appearance of a keloid scar, which is a pathological scar characterized by a fold of fibrous consistency, or by skin retractions resulting in a loss of elasticity of the skin. The healing phase takes place in 5 stages: the first phase is the inflammatory phase, which is the starting point for the tissue repair. This inflammatory reaction causes vasodilation and increases the permeability of the lesion. The second phase is the angiogenesis phase, which enables the provision of nutrients and oxygen, essential to the cells. The third phase is the migration phase: the renewal (and therefore granulation) tissue is put in place: this is the beginning of the production of the scar. All the connective tissue cells migrate to the centre of the lesion, in particular the fibroblasts and the keratinocytes. The fourth phase is the proliferation phase, which consists of a massive proliferation of the connective tissue cells, and of fibres associated with blood vessel development. The final phase is the maturation phase, which is the longest phase: it lasts from 18 to 24 days. The number of fibroblasts will then decrease, as will the number of blood vessels, so as to result in the end of healing. In the case of diabetic patients, healing is a slow and difficult process which exposes them to chronic wounds that are extremely difficult to heal, often becoming complicated by infectious phenomena which can secondarily lead to amputations. By virtue of their pleiotropic activities, FGFs participate in tissue repair in particular by activating keratinocytes and fibroblasts and by participating in the angiogenesis phenomenon. Thus, FGFs appear to play a role in improving healing in healthy or diabetic patients, both from the point of view of the rapidity of healing and from the point of view of scar quality. It has also been clearly described that the levels of growth factors involved in healing phenomena, and in particular FGFs, decrease very greatly with age. Thus, in elderly patients, the deficiencies and delays in healing are linked to deficiencies in FGFs in the skin.

Glutamate is a putative transmitter of dorsal ganglion neurons and bradykinin is a molecule produced during inflammation that can activate and sensitize nociceptive fibres. In this context, FGF2 could modulate inflammatory pain even though no regulatory effect of FGF2 on nociceptive fibres has been demonstrated in vivo. However, it has been demonstrated that FGF2 completely blocks bradykinin-stimulated glutamate release in vitro (Rydh-Rinder et al. (2001) Regul Pept 102:69-79). Thus, FGFs could play a role in nociception and chronic pain.

Peripheral neuropathy is axonal or demyelinating damage to the motor and/or sensory peripheral nerve that leads to desensitization of the distal limbs. One of the consequences of the nerve damage may be a perforating ulcer, which is to be particularly feared when there is considerable damage to the profound sensitivity since, in this case, the body's weight has a tendency to always be carried by the same support points. One of the major secondary complications of diabetes is the chronic development of peripheral neuropathy. In this context, it has been demonstrated that FGF2 induces axonal regeneration that could be a therapy of choice in the treatment of peripheral nerve damage and therefore in peripheral neuropathy (Basic fibroblast growth factor isoforms promote axonal elongation and branching of adult sensory neurons in vitro. Klimaschewski L, Nindl W, Feurle J, Kavakebi P, Kostron H. Neuroscience. 2004; 126(2):347-53).

It has been proposed that the FGF system is an essential system of muscle regeneration, and of myoblast survival and proliferation (Neuhaus, P. et al. Reduced mobility of fibroblast growth factor (FGF)-deficient myoblasts might contribute to dystrophic changes in the musculature of FGF2/FGF6/mdx triple-mutant mice. Mol Cell Biol 23, 6037-48, 2003). FGF2 could be exploited in order to promote muscle regeneration, in particular in the case of sarcopenia, of loss of smooth muscle functionality in the sphincters, and also for the survival and progression of transplanted myoblasts, and in particular in Duchenne muscular dystrophy. Growth factors such as VEGF or FGF2 also appeared to improve myocardial perfusion after ischaemia (Hendel, R. C. et al. Effect of intracoronary recombinant human vascular endothelial growth factor on myocardial perfusion: evidence for a dose-dependent effect. Circulation 101, 118-21, 2000). Furthermore, the vascular network is essential to tissue development and preservation. By promoting the delivery of nutrients, oxygen and cells, the blood vessels assist in maintaining the functional and structural integrity of tissues. In this context, angiogenesis and vasculogenesis make it possible to preserve and perfuse tissues after ischaemia. Angiogenic growth factors such as FGF2 thus promote revascularization for tissue regeneration. Thus, FGF2, by acting directly on skeletal muscle cells and on angiogenesis, would have an effect on the regeneration of dystrophic or normal muscles (Fibbi, G., D'Alessio, S., Pucci, M., Cerletti, M. & Del Rosso, M. Growth factor-dependent proliferation and invasion of muscle satellite cells require the cell-associated fibrinolytic system. Biol Chem 383, 127-36, 2002).

Among the main growth factors, it is now clearly established that systemic administration of FGF2 facilitates bone repair after fracture (Acceleration of fracture healing in non-human primates by fibroblast growth factor-2. Kawaguchi H, Nakamura K, Tabata Y, Ikada Y, Aoyama I, Anzai J, Nakamura T, Hiyama Y, Tamura M. J Clin Endocrinol Metab. 2001 February; 86(2), 875-880). The local application of FGF2 in gelatin matrices accelerates bone repair in primates, suggesting the clinical usefulness of FGF2 in the treatment of fractures.

The endogenous overregulation of FGF7 (or KGF) and of FGF18 appears to be an important mechanism for promoting the proliferation, migration and protection of hair follicles in pathological cases or following treatment with a cytotoxic agent (Comprehensive Analysis of FGF and FGFR Expression in Skin: FGF18 Is Highly Expressed in Hair Follicles and Capable of Inducing Anagen from Telogen Stage Hair Follicles. Mitsuko Kawano, Akiko Komi-Kuramochi, Masahiro Asada, Masashi Suzuki, Junko Oki, Ju Jiang and Toru Imamura).

The applicant has now found novel synthetic molecules capable of inducing FGF receptor dimerization and which can be of use in numerous mechanisms where FGFRs are involved, such as angiogenesis, or smooth muscle, bone or hair-follicle cell regeneration.

The objective of the invention is to propose novel FGF receptor agonist compounds with a dimeric structure.

These compounds bring about dimerization of FGF receptors, which causes their activation and, in the end, cell activation.

A subject of the present invention is FGF receptor agonist compounds corresponding to the general formula:

$$M_1\text{-}L\text{-}M_2$$

in which $M_1$ and $M_2$, which may be identical or different, each represent, independently of one another, a monomer unit M and L represents a linker group which links $M_1$ and $M_2$ covalently.

The agonists of formula $M_1$-L-$M_2$ according to the invention comprise two monomer units of general formula M, called $M_1$ and $M_2$, which may be identical different, chosen as each having an FGFR antagonist activity.

A subject of the present invention is FGF receptor agonist compounds of formula $M_1$-L-$M_2$ as defined above, characterized in that said monomer unit $M_1$ and $M_2$ corresponds to the general formula M which follows:

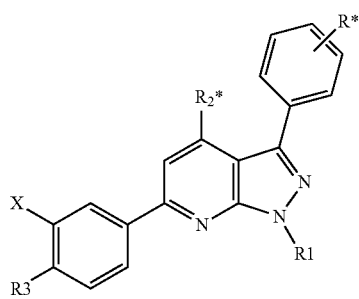

in which,
the asterisk * indicates the site of linkage between the monomer unit M and the linker L, said linkage site of each monomer unit $M_1$ and $M_2$ being located on one of the substituents R or $R_2$,
R represents a hydrogen atom (in which case the site of linkage of L with M is located on $R_2$) or a group —CONH*,
$R_1$ represents a hydrogen atom or a linear ($C_1$-$C_3$)alkyl group,
$R_2$ represents a group —$CONH_2$ (in which case the site of linkage of L with M is located on R) or —CONH*,
$R_3$ represents a group —$CO_2R_4$, where $R_4$ represents a hydrogen atom or a linear ($C_1$-$C_4$)alkyl group,
X is a halogen atom chosen from fluorine, chlorine and bromine atoms,
in the form of a base or of an addition salt with an acid or with a base.

L represents a linker group which links $M_1$ and $M_2$ covalently in such a way that the distance between the two monomer units $M_1$ and $M_2$ allows the dimerization of two FGF receptors. Said linker group preferably comprises from 11 to 20 links. Said linker group L more particularly comprises from 12 to 16 links. The term "links" is intended to mean only the bonds between atoms which make it possible to connect the monomer units $M_1$ et $M_2$.

The linker group L is characterized by a flexibility which enables each monomer unit of the compound of formula $M_1$-L-$M_2$ to establish contact with the extracellular binding sites of the FGFR transmembrane receptors.

L is attached, firstly, to a monomer unit of formula $M_1$ by an atom placed on any one of the substituents R or $R_2$ and attached, secondly, to the other monomer unit of formula $M_2$ by an atom placed on any one of the substituents R or $R_2$, with $M_1$ and $M_2$ being identical or different.

In the aforementioned, a subject of the present invention is also compounds as defined above, characterized in that:
L connects the 2 monomer units $M_1$ and $M_2$ via the radical R; or
L connects the 2 monomer units $M_1$ and $M_2$ via the radical $R_2$; or
L connects the 2 monomer units $M_1$ and $M_2$ via the radical R in its para position; or
L connects the 2 monomer units $M_1$ and $M_2$ via the radical R in its meta position.

These compounds of formula $M_1$-L-$M_2$ can exist in the form of bases or in a form salified with acids or bases, in particular pharmaceutically acceptable acids or bases. Such addition salts are part of the invention. These salts are advantageously prepared with pharmaceutically acceptable acids or bases, but the salts of other acids or bases which are of use, for example, for purifying or isolating the compounds of the invention are also part of the invention.

In the context of the present invention, and unless otherwise mentioned in the text:
the term alkyl is intended to mean: a linear or branched, saturated hydrocarbon-based aliphatic group comprising from 1 to 6 carbon atoms;
the term halogen is intended to mean: a chlorine, fluorine, bromine or iodine atom;
the term aryl is intended to mean: a cyclic aromatic group comprising between 5 and 10 carbon atoms, for example a phenyl group, optionally substituted with one or more ester groups and/or a halogen atom.

A subject of the present invention is particularly compounds as defined above, comprising the monomer unit of formula M in which $R_1$ represents a hydrogen atom, in the form of a base or of an addition salt with an acid or with a base.

A subject of the present invention is particularly compounds as defined above, comprising the monomer unit of formula M in which $R_3$ represents a group —$CO_2R_4$, with $R_4$ representing a hydrogen atom, in the form of a base or of an addition salt with an acid or with a base.

A subject of the present invention is particularly compounds as defined above, comprising the monomer unit of formula M in which X represents a fluorine atom, in the form of a base or of an addition salt with an acid or with a base.

A subject of the present invention is particularly compounds as defined above, comprising the monomer unit of formula M in which:
R represents a group —CONH*, where the asterisk * indicates the site of linkage of L, firstly, with the monomer unit $M_1$ and, secondly, with the monomer unit $M_2$; advantageously, R is located in the meta or para position,
$R_1$ represents a hydrogen atom or a linear ($C_1$-$C_3$)alkyl group and advantageously a hydrogen atom,
in the form of a base or of an addition salt with an acid or with a base.

A subject of the present invention is particularly compounds as defined above, comprising the monomer unit of formula M in which:
$R_1$ represents a hydrogen atom,
$R_2$ represents a group —CONH*, where the asterisk * indicates the site of linkage of L, firstly, with the monomer unit $M_1$ and, secondly, with the monomer unit $M_2$,
in the form of a base or of an addition salt with an acid or with a base.

A subject of the present invention is in particular FGF receptor agonist compounds of formula $M_1$-L-$M_2$, characterized in that said monomer units $M_1$ and $M_2$, which are identical, correspond to the general formula M in which:
R represents a hydrogen atom (in which case the site of linkage of L with M is located on $R_2$) or a group —CONH*,
$R_1$ represents a hydrogen atom,
$R_2$ represents a group —$CONH_2$ (in which case the site of linkage of L with M is located on R) or —CONH*,
$R_3$ represents a group —$CO_2R_4$, where $R_4$ represents a hydrogen atom,
X is a fluorine atom,
in the form of a base or of an addition salt with an acid or with a base.

The linker group L can be more particularly chosen from the following PEG radicals:

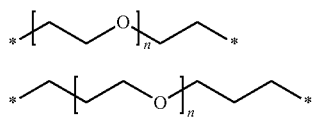

(A)

(B)

in which
the asterisk * indicates the atom for linkage of L with the monomer unit M on the substituent R* or $R_2$*;
n represents an integer from 2 to 6, advantageously n represents an integer from 2 to 5 and more advantageously 3 or 4,
these compounds being optionally present in the form of a base or of an addition salt with an acid or with a base.
The subgroups defined above, taken separately or in combination, also form part of the invention.

Among the compounds of formula $M_1$-L-$M_2$, which are subject of the invention, mention may in particular be made of the following compounds in the order of the compounds of the table hereinafter:
Compound No. 1: 3,3'-{ethane-1,2-diylbis[oxypropane-3,1-diylcarbamoyl(3-phenyl-1H-pyrazolo[3,4-b]pyridine-4,6-diyl)]}bis(6-fluorobenzoic acid);
Compound No. 2: 5-[4-({15-[6-(3-carboxy-4-fluorophenyl)-3-phenyl-1H-pyrazolo[3,4-b]pyridin-4-yl]-15-oxo-4,7,10-trioxa-14-azapentadec-1-yl}carbamoyl)-3-phenyl-1H-pyrazolo[3,4-b]pyridin-6-yl]-2-fluorobenzoic acid;
Compound No. 3: 5-[4-({16-[6-(3-carboxy-4-fluorophenyl)-3-phenyl-1H-pyrazolo[3,4-b]pyridin-4-yl]-16-oxo-3,6,9,12-tetraoxa-15-azahexadec-1-yl}carbamoyl)-3-phenyl-1H-pyrazolo[3,4-b]pyridin-6-yl]-2-fluorobenzoic acid;
Compound No. 4: 5-[4-({19-[6-(3-carboxy-4-fluorophenyl)-3-phenyl-1H-pyrazolo[3,4-b]pyridin-4-yl]-19-oxo-3,6,9,12,15-pentaoxa-18-azanonadec-1-yl}carbamoyl)-3-phenyl-1H-pyrazolo[3,4-b]pyridin-6-yl]-2-fluorobenzoic acid;
Compound No. 5: 5-[4-({21-[6-(3-carboxy-4-fluorophenyl)-3-phenyl-1H-pyrazolo[3,4-b]pyridin-4-yl]-21-oxo-4,7,10,13,16-pentaoxa-20-azahenicos-1-yl}carbamoyl)-3-phenyl-1H-pyrazolo[3,4-b]pyridin-6-yl]-2-fluorobenzoic acid;
Compound No. 6: 5-(4-carbamoyl-3-{3-[(15-{3-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid;
Compound No. 7: 3,3'-{ethane-1,2-diylbis[oxyethane-2,1-diylcarbamoylbenzene-3,1-diyl(4-carbamoyl-1H-pyrazolo[3,4-b]pyridine-3,6-diyl)]}bis(6-fluorobenzoic acid);
Compound No. 8: 5-(4-carbamoyl-3-{4-[(15-{4-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid;
Compound No. 9: 3,3'-{ethane-1,2-diylbis[oxyethane-2,1-diylcarbamoylbenzene-4,1-diyl(4-carbamoyl-1H-pyrazolo[3,4-b]pyridine-3,6-diyl)]}bis(6-fluorobenzoic acid).

The present invention also relates to a process for preparing dimers of formula $M_1$-L-$M_2$ comprising the reaction of at least one reactant of a monomer unit of formula M which has a carboxylic acid function with a reactant of formula $H_2$N-L-$NH_2$ where M and L have the same meaning as previously.

In what follows, the term "protective group PG" is intended to mean a group which makes it possible, firstly, to protect a reactive function such as a hydroxyl or a carboxylic acid during a synthesis and, secondly, to regenerate the intact reactive function at the end of synthesis. Examples of protective groups and also methods of protection and of deprotection are given in «Protective Groups in Organic Synthesis», Green et al., $4^{th}$ Edition (John Wiley & Sons, Inc., New York).

In what follows, the term "leaving group" is intended to mean a group which can be easily cleaved from a molecule by breaking a heterolytic bond, with the departure of a pair of electrons. This group can thus be easily replaced with another group in a substitution reaction, for example. Such leaving groups are, for example, halogens or an activated hydroxyl group, such as a mesyl, tosyl, triflate, acetyl, para-nitrophenyl, etc. Examples of leaving groups and also methods for preparing them are given in «Advanced Organic Chemistry», J. March, $5^{st}$ Edition, Wiley Interscience, p. 310-316.

In accordance with the invention, the compounds of the invention can be prepared according to the processes hereinafter.

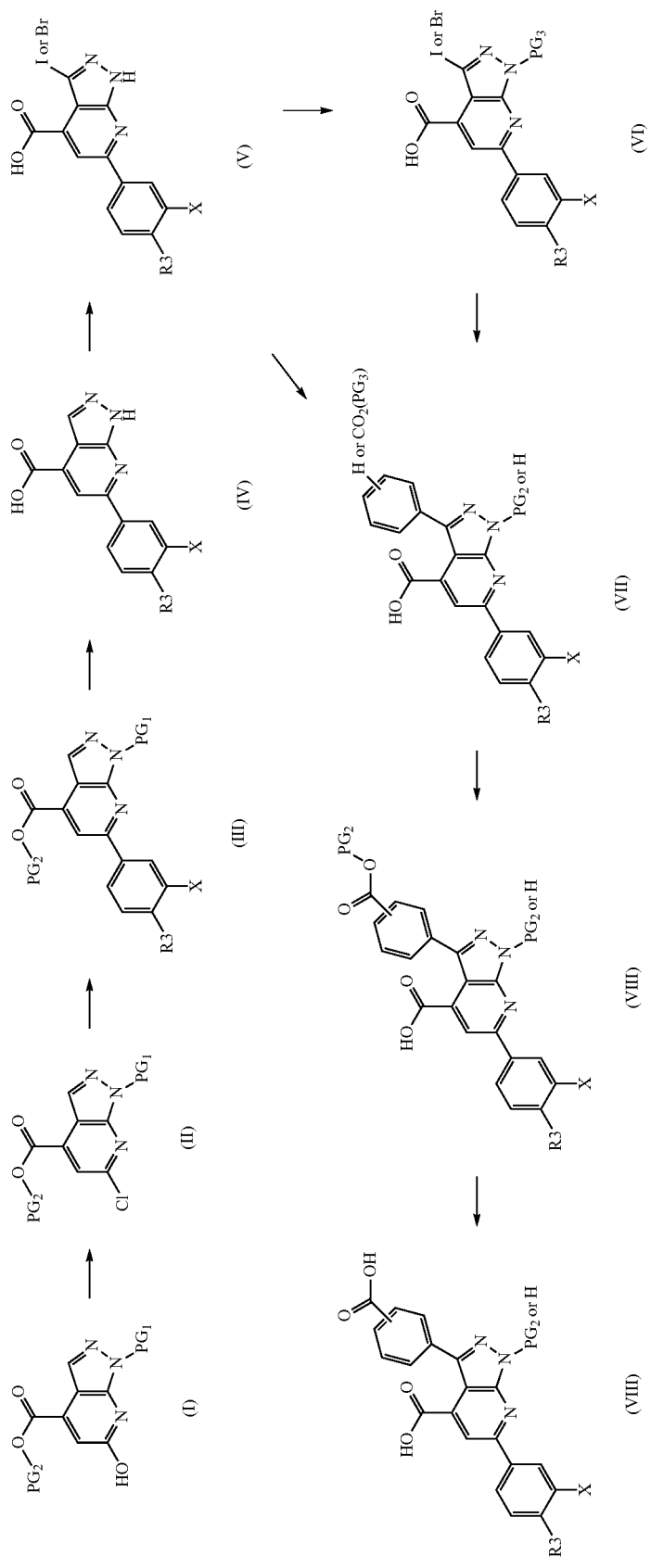

Scheme 1 illustrates the synthesis of the monomers of formulae (VII) and (IX). The 6-hydroxy-1H-pyrazolo[3,4-b]pyridine-4-carboxylic acid derivative of formula (I) protected with $PG_1$, which is a protective group such as, for example, Bn or PMB, and $PG_2$, which is a group Alk or Bn or PMB, is obtained according to or after adaptation of the process described by H. Dorn and T. Mueller, *Zeitschrift fuer Chemie*, 1980, 20(3), 95. The hydroxy derivative of formula (I) reacts with $POCl_3$ in an inert solvent such as DMF while heating at from 60 to 100° C. so as to give the protected derivative of 6-chloro-1H-pyrazolo[3,4-b]pyridine-4-carboxylic acid of formula (II) with $PG_1$ and $PG_2$ as defined previously. The compound of formula (II) is used in an organometallic coupling reaction catalyzed with palladium, using for example $Pd(PPh_3)_4$, with either aryl boronic acids or esters in the presence of a weak base, such as, for example, caesium carbonate, in an inert solvent such as DMF, while heating at 60-120° C. so as to give the compound of formula (III) with $R_3$ representing an ester. The compound of formula (III) is subjected to operating conditions which make it possible to selectively deprotect the pyrazole and the carboxylic acid in position 4, such as acidic conditions with, for example, concentrated sulphuric acid while heating at 40-60° C. or hydrogenolysis with Pd/C so as to give the compound of formula (IV). The regioselective introduction of a halogen atom in position 3 of the 1H-pyrazolo[3,4-b]pyridine derivative of formula (IV) is carried out via an aromatic electrophilic substitution reaction with reactants such as, for example, iodine, NIS, NBS or bromine, optionally in the presence of a weak base such as $NaHCO_3$ in an inert solvent such as anhydrous or aqueous MeOH, dioxane or DCM, at ambient temperature, so as to give the halogenated derivative of formula (V). The pyrazole of the compound of formula (V) can be selectively protected with a protective group $PG_3$ such as, for example, a THP using DHP in a solvent such as DMF at ambient temperature in the presence of a catalytic amount of an acid, such as, for example, APTS, so as to give the compound of formula (VI).

The compounds of formula (V) or (VI) can be subjected to an organometallic coupling reaction catalyzed with palladium using, for example, $Pd(PPh_3)_4$ or $Pd(OAc)_2$ or $PdCl_2$(dppf), with either aryl boronic acids or esters or aryl trialkylstannane derivatives in the presence of a ligand such as, for example, sodium 2'-dicyclohexylphosphino-2,6-dimethoxy-1,1'-biphenyl-3-sulphonate hydrate, optionally in the presence of a weak base, such as, for example, potassium carbonate, in an inert solvent such as DMF, while heating at 60-120° C. so as to give the compound of formula (VII).

The carboxylic acids of formula (VII) which have a substituent —$CO_2(PG_4)$ with $PG_4$ being a Bn group or PMB group or tert-butyl group, with or without a protective group $PG_3$, such as, for example, THP, can be activated in anhydride form with, for example, $Boc_2O$ or in activated ester form with, for example, PyBop, and can then react with aqueous ammonia or a derivative of aqueous ammonia, so as to give the amides of formula (VIII). Treatment of the compounds of formula (VIII) in an acidic medium with, for example, concentrated sulphuric acid at ambient temperature or under hydrogenolysis conditions with Pd/C, gives the carboxylic acids of formula (IX). The linear alkyl substituent $R_1$ is inserted by nucleophilic substitution reaction under the reaction conditions well known to those skilled in the art.

Scheme 2: preparation of the dimers

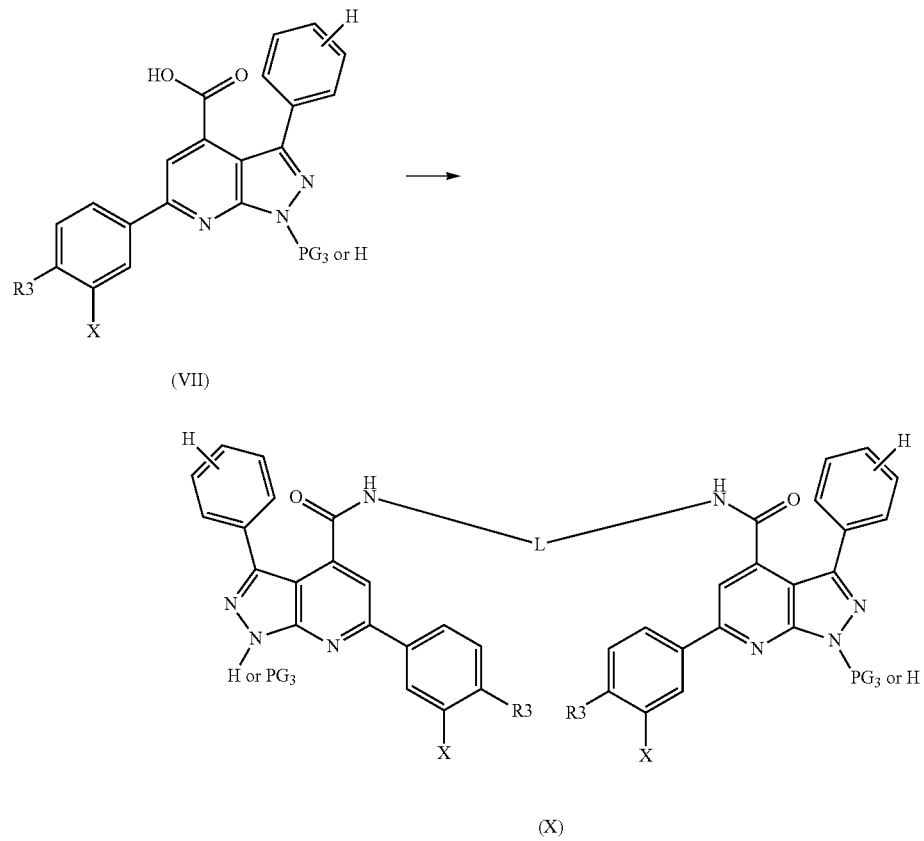

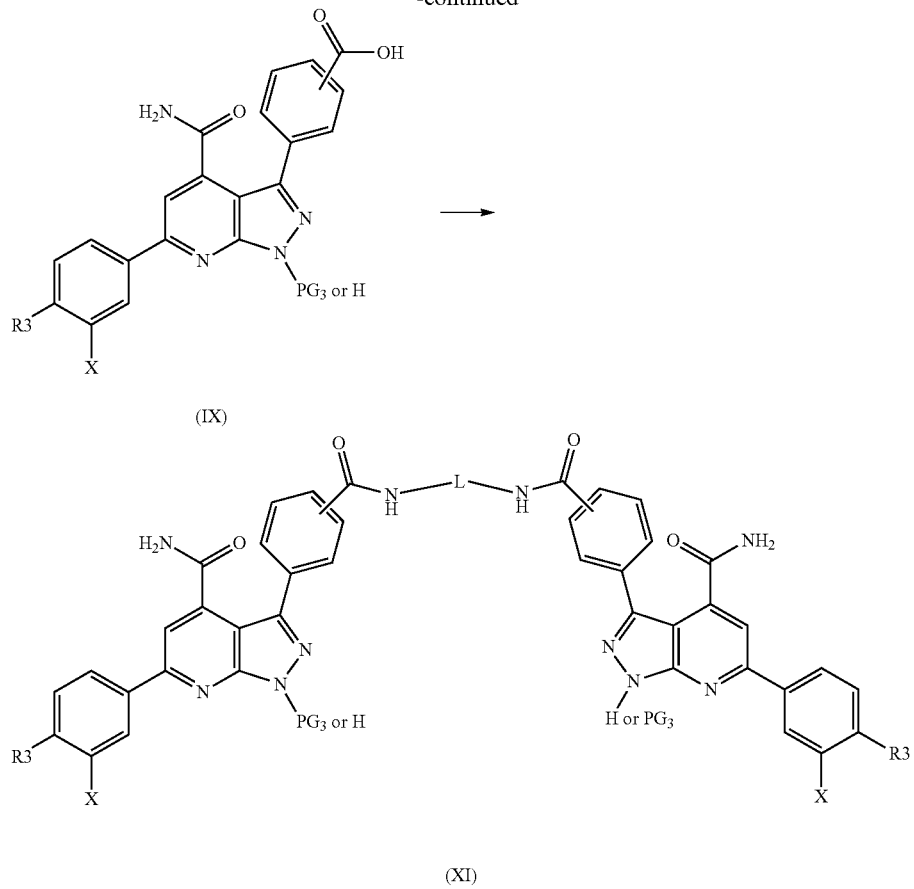

(IX)

(XI)

Scheme 2 illustrates the preparation of the dimers of the invention. The carboxylic acids of formulae (VII) and (IX) are coupled to a diamine of formula $H_2N-L-NH_2$ after activation with, for example, PyBop in the presence of a weak base, such as triethylamine in a solvent such as THF or DMF, at ambient temperature, so as to give the dimers of formulae (X) and (XI) respectively. Saponification of the esters $R_3$ in the compounds of formulae (X) and (XI) respectively gives the compounds of the invention. When the pyrazole of the compounds of formulae (X) and (XI) is protected with a protective group $PG_3$, an additional step, such as a treatment in an acidic medium with, for example, TFA under dry conditions is necessary before or after the saponification of $R_3$ in order to obtain the compounds of the invention.

In schemes 1 and 2 above, the starting compounds, the intermediates and the reactants, when the method for preparing them is not described, are commercially available or described in the literature, or can be prepared according to methods which are described therein or which are known to those skilled in the art.

According to another of its aspects, a subject of the invention is also the compounds of formulae (II) to (XI) defined above. These compounds are of use as synthesis intermediates for the compounds of the invention.

The following examples describe the preparation of certain compounds in accordance with invention. These examples are not limiting and merely illustrate the present invention. The numbers of the compounds exemplified refer to those given in the table hereinafter, which shows the chemical structures and the physical properties of some compounds according to the invention.

The following abbreviations and molecular formulae are used:
PTSA=para-toluenesulphonic acid
EtAOc=ethyl acetate
Bn=benzyl
$Boc_2O$=di-tert-butyl dicarbonate
DCM=dichloromethane
DHP=dihydropyran
DMF=N,N-dimethylformamide
EtOH=ethanol
h=hour(s)
$KHSO_4$=potassium hydrogen sulphate
LCMS=Liquid Chromatography Mass Spectroscopy
MeOH=methanol
MeTHF=2-methyltetrahydrofuran
min=minute(s)
mL=milliliter(s)
(m) mol=(milli)mol(s)
$NaHCO_3$=Sodium hydrogen carbonate
NBS=N-bromosuccinimide
NIS=N-iodosuccinimide
$Pd(PPh_3)_4$=tetrakis(triphenylphosphine)palladium(0)
PMB=para-methoxybenzyl group
ppm=parts per million
PyBop=benzotriazol-1-yloxytrispyrrolidinophosphonium hexafluorophosphate
NMR=nuclear magnetic resonance
RT=retention time TFA=trifluoroacetic acid
THF=tetrahydrofuran
THP=tetrahydropyranyl group In what follows:

proton magnetic resonance ($^1$H NMR) spectra, as described below, are recorded at 250 MHz or 500 MHz in DMSO-$d_6$, using the DMSO-$d_6$ peak as a reference. The chemical shifts δ are expressed in parts per million (ppm). The signals observed are expressed in the following way: s=singlet; d=doublet; t=triplet; m=multiplet or br.s.=broad singlet;

the LCMS characteristics, as described below, indicate successively the analytical method of high-performance liquid chromatography used and detailed below (methods 1 to 8), the [M+H]$^+$ peak identified by mass spectrometry and the retention time RT of the compound, expressed in minutes.

Method 1
Instrument: HPLC system of the 1100 (Agilent) or Alliance (Waters) type; simple quadrupole mass spectrometer of the MSD (Agilent) or ZQ (Waters) type
Column: Waters Symmetry C18 3.5 µm (2.1×50 mm)
Solvent A: H$_2$O+0.005% TFA; Solvent B: CH$_3$CN+0.005% TFA
Flow rate: 0.4 mL/min
Gradient A/B: 100/0 (t0 min) to 0/100 (t10 min) to 0/100 (t15 min)
Detection: UV 220 nm
Ionization: positive electrospray mode ESI+
Method 2=method 1 with change of gradient
Gradient A/B: 100/0 (t0 min) to 0/100 (t30 min) to 0/100 (t35 min)

Method 3
Instrument: HPLC system of the 1100 (Agilent) or Alliance (Waters) type; simple quadrupole mass spectrometer of the MSD (Agilent) or ZQ (Waters) type
Column: Waters X Terra C18 3.5 µm (2.1×50 mm)
Solvent A: H$_2$O+10 mM AcONH$_4$, pH7; Solvent B: CH$_3$CN
Flow rate: 0.4 mL/min
Gradient A/B: 100/0 (t0 min) to 10/90 (t10 min) to 10/90 (t15 min)
Detection: UV 220 nm
Ionization: positive electrospray mode ESI+
Method 4=method 3 with change of gradient
Gradient A/B: 100/0 (t0 min) to 10/90 (t30 min) to 10/90 (t35 min)

Method 5
Instrument: HPLC system of the 1100 (Agilent) or Alliance (Waters) type; simple quadrupole mass spectrometer of the MSD (Agilent) or ZQ (Waters) type
Column: Waters Symmetry C18 3.5 µm (2.1×50 mm)
Solvent A: H$_2$O+0.05% TFA; Solvent B: CH$_3$CN+0.035% TFA
Flow rate: 0.5 mL/min
Gradient A/B: 100/0 (t0 min) to 0/100 (t7 min)
Detection: UV 220 nm
Ionization: positive electrospray mode ESI+

Method 6
Instrument: HPLC system of the 1100 (Agilent) or Alliance (Waters) type; simple quadrupole mass spectrometer of the MSD (Agilent) or ZQ (Waters) type
Column: Phenomenex Luna C18(2)-HST (30×2 mm) 2.5 µm; column temp.: 50° C.
Solvent A: H$_2$O+0.05% TFA; Solvent B: CH$_3$CN+0.035% TFA
Flow rate: 1 mL/min
Gradient A/B: 100/0 (t0 min) to 0/100 (t2.5 min) to 0/100 (t3.5 min)
Detection: UV 220 nm
Ionization: positive electrospray mode ESI+
Method 7
Instrument: Waters UPLC
Column: BEH C18 (2.1×50 mm) 1.7 µm; column temp.: 55° C.
Solvent A: H$_2$O+0.1% HCO$_2$H; Solvent B: CH$_3$CN+0.08% HCO$_2$H
Flow rate: 0.9 mL/min
Gradient A/B: 95/5 (t0 min) to 5/95 (t1.1 min) to 5/95 (t1.7 min)
Detection: 220 nM
Ionization: positive electrospray mode ESI+
Method 8
Instrument: Waters UPLC
Column: Waters XBridge C18 (4.6×50 mm) 2.5 µm
Solvent A: H$_2$O+0.1% TFA; Solvent B: CH$_3$CN+0.1% TFA
Gradient A/B: 97/3 (t0 min) to 40/60 (t3.5 min) to 2/98 (t4 min) to 2/98 (t5 min)
Detection: 220 nM
Ionization: positive electrospray mode ESI+

EXAMPLE 1

Lysine Salt of 5-[4-({15-[6-(3-carboxy-4-fluorophenyl)-3-phenyl-1H-pyrazolo[3,4-b]pyridin-4-yl]-15-oxo-4,7,10-trioxa-14-azapentadec-1-yl}carbamoyl)-3-phenyl-1H-pyrazolo[3,4-b]pyridin-6-yl]-2-fluorobenzoic acid (Compound No. 2)

Step 1.1 ethyl 1-benzyl-6-chloro-1H-pyrazolo[3,4-b]pyridine-4-carboxylate

Phosphoryl trichloride (74 mL/0.81 mol) is added dropwise to a solution of ethyl 1-benzyl-6-hydroxy-1H-pyrazolo[3,4-b]pyridine-4-carboxylate [CAS 74439-45-5] (40.0 g/0.135 mol) in 450 mL of DMF at 0° C. under nitrogen. The reaction medium is stirred at 80° C. for 24 hours so as to give a dark brown solution. It is then run into a mixture of ice-cold water, and extracted with EtOAc. The organic phase is washed with water, dried with sodium sulphate, filtered and concentrated to dryness. The solid obtained is taken up with isopropanol, filtered, washed with diisopropyl ether and oven-dried to give 30.6 g of a yellow powder (yield: 72%).

LCMS (method 1): [M+H]$^+$=316.1, RT=9.34 min

Step 1.2. 1-benzyl-6-chloro-1H-pyrazolo[3,4-b]pyridine-4-carboxylic acid

A molar solution of sodium hydroxide (116 mL/0.116 mol) is added to a solution of ethyl 1-benzyl-6-chloro-1H-pyrazolo[3,4-b]pyridine-4-carboxylate (30.5 g/96.8 mmol) in 195 mL of THF. The mixture is stirred at ambient temperature for 2 hours and then run into a saturated aqueous solution of NaHCO$_3$. The aqueous phase is washed with ethyl acetate and then acidified with a solution of KHSO$_4$ (1 M) and extracted with EtOAc. The organic phase is dried over sodium sulphate and then concentrated to dryness. The product is taken up with diisopropyl ether, filtered, and then dried under vacuum to give 27.3 g of a pale yellow powder (yield: 98%).

LCMS (method 1): [M+H]$^+$=288.1, RT=7.59 min

Step 1.3 benzyl 1-benzyl-6-chloro-1H-pyrazolo[3,4-b]pyridine-4-carboxylate

Benzyl bromide (11 mL/89 mol) is added dropwise to a suspension of 1-benzyl-6-chloro-1H-pyrazolo[3,4-b]pyridine-4-carboxylic acid (27.0 g/93.9 mmol) and potassium carbonate (15.6 g/112 mmol) in 310 mL of DMF. The mixture is stirred at ambient temperature for 2 hours and then run into a saturated aqueous solution of ice-cold $NaHCO_3$. The precipitate formed is filtered, thoroughly washed with water, and dried under vacuum to give 32.6 g of a pale yellow powder (yield: 92%).

LCMS (method 1): $[M+H]^+$=378.0, RT=10.20 min

Step 1.4 benzyl 1-benzyl-6-[4-fluoro-3-(methoxycarbonyl)phenyl]-1H-pyrazolo[3,4-b]pyridine-4-carboxylate The catalyst $Pd(t-BuP)_2$ (2.03, 3.97 mmol) or $Pd(PPh_3)_4$ (4.58 g/4.0 mmol) is added to a suspension of benzyl 1-benzyl-6-chloro-1H-pyrazolo[3,4-b]pyridine-4-carboxylate (15.0 g/40 mol), 3-fluoro-3-methoxycarbonylphenylboronic acid (15.7 g/79 mol) and caesium carbonate (25.9 g/0.079 mol) in 125 mL of anhydrous DMF under argon. The mixture is stirred at 80° C. for 2 hours under argon. The reaction mixture is hot-filtered through talc, run into a saturated aqueous solution of $NaHCO_3$ and extracted with EtOAc. After separation of the two phases, the organic phase is washed with water, dried over sodium sulphate and then concentrated until the first crystals appear. The crystalline product is filtered, washed with diisopropyl ether, and then dried under vacuum. The filtrate is run into a DCM/cyclohexane (50/50) mixture and the precipitate obtained is filtered and dried under vacuum. The two batches are combined to give 12.3 g of a yellow powder (yield: 62%).

LCMS (method 5): $[M+H]^+$=496.4, RT=6.88 min

Step 1.5 1-benzyl-6-[4-fluoro-3-(methoxycarbonyl)phenyl]-1H-pyrazolo[3,4-b]pyridine-4-carboxylic acid Benzyl 1-benzyl-6-[4-fluoro-3-(methoxycarbonyl)phenyl]-1H-pyrazolo[3,4-b]pyridine-4-carboxylate (12.0 g/24.2 mmol) is dissolved in 100 mL of concentrated sulphuric acid. The solution is heated at 50° C. for 1 hour. The reaction mixture is then slowly run into ice-cold water and extracted with EtOAc. The organic phase is washed with water and then with a saturated aqueous solution of NaCl, dried over sodium sulphate and concentrated to dryness to give 6.25 g of a yellow-orange powder (yield: 82%).

LCMS (method 1): $[M+H]^+$=316.2, RT=6.80 min

Step 1.6 1-benzyl-6-[4-fluoro-3-(methoxycarbonyl)phenyl]-3-iodo-1H-pyrazolo[3,4-b]pyridine-4-carboxylic acid Sodium hydrogen carbonate (11.39 g/0.136 mol) and N-iodosuccinimide (30.51 g/0.136 mol) are added portionwise to a suspension of 1-benzyl-6-[4-fluoro-3-(methoxycarbonyl)phenyl]-1H-pyrazolo[3,4-b]pyridine-4-carboxylic acid (14.25 g/45.2 mmol) in 410 mL of dioxane. The reaction mixture is stirred for 24 h at ambient temperature. The reaction medium is run into a saturated aqueous solution of $NaHCO_3$. The aqueous phase is washed with EtOAc and then acidified to pH=2-3 using a solution of $KHSO_4$ (1 M), and extracted with EtOAc. The organic phase is washed with water, with a solution of sodium thiosulphate (0.1 M) and with a saturated aqueous solution of NaCl, dried over sodium sulphate and then concentrated to dryness to give 13.9 g of a yellow powder (yield: 70%).

LCMS (method 6): $[M+H]^+$=442.3, RT=1.92 min

Step 1.7 6-[4-fluoro-3-(methoxycarbonyl)phenyl]-3-iodo-1-(tetrahydro-2H-pyran-2-yl)-1H-pyrazolo[3,4-b]pyridine-4-carboxylic acid para-Toluenesulphonic acid (38 mg/0.20 mmol) and 3,4-dihydro-2H-pyran (2.75 mL/30.1 mmol) are added successively to a solution of 1-benzyl-6-[4-fluoro-3-(methoxycarbonyl)phenyl]-3-iodo-1H-pyrazolo[3,4-b]pyridine-4-carboxylic acid (4.43 g/10.0 mmol) in 50 mL of DCM. The solution is stirred at ambient temperature for 12 hours. The reaction medium is run into a solution of $KHSO_4$ (1 M) and extracted with EtOAc. The organic phase is washed with water and with a saturated aqueous solution of NaCl, dried over sodium sulphate, filtered and concentrated to dryness. The brown gum obtained is dissolved in 75 mL of DCM and added to the TEA scavenger resin (FL-TEA, Polymerlab, Variant, 3.53 mmol/g) (3.3 g/11 mmol). After stirring at ambient temperature for 2 h, the resin is filtered and washed with DCM. After drying under vacuum, the resin is then stirred for 20 minutes in a solution of triethylamine (2.6 mL/18 mmol) in 90 mL of DCM and then filtered and rinsed with DCM. The filtrate is acidified with a solution of $KHSO_4$ (1 M). After extraction with EtOAc, the organic phase is washed with water and with a saturated aqueous solution of NaCl, dried over sodium sulphate, filtered and concentrated to dryness to give 4.3 g of an orange powder (yield: 82%).

LCMS (method 1): $[M+H]^+$=526.8, RT=8.78 min

Step 1.8 6-[4-fluoro-3-(methoxycarbonyl)phenyl]-3-phenyl-1-(tetrahydro-2H-pyran-2-yl)-1H-pyrazolo[3,4-b]pyridine-4-carboxylic acid The ligand sodium 2'-dicyclohexylphosphino-2,6-dimethoxy-1,1'-biphenyl-3-sulphonate hydrate (84 mg/0.17 mmol) and the catalyst $Pd(OAc)_2$ (185 mg/0.83 mmol) are added to a solution of 6-[4-fluoro-3-(methoxycarbonyl)phenyl]-3-iodo-1-(tetrahydro-2H-pyran-2-yl)-1H-pyrazolo[3,4-b]pyridine-4-carboxylic acid (0.865 g/1.65 mmol) and of tributylphenylstannane (1.61 mL/4.94 mmol) in 11 mL of anhydrous DMF placed in a microwave reactor under argon. The reactor is sealed and the mixture is heated for 20 min at 130° C. in a microwave. The reaction medium is cooled and filtered through talc, before being concentrated to dryness. After purification by flash chromatography on silica (DCM/EtOAc: 90/10 to 80/20 then cyclohexane/EtOH 1% TEA: 95/5 to 70/30), 525 mg of an orange powder are obtained (yield: 67%).

LCMS (method 1): $[M+H]^+$=476.0, RT=9.13 min

Step 1.9 6-[4-fluoro-3-(methoxycarbonyl)phenyl]-3-phenyl-1H-pyrazolo[3,4-b]pyridine-4-carboxylic acid 10 mL of a solution of anhydrous hydrogen chloride in dioxane (4 M) are added to a solution of 6-[4-fluoro-3-(methoxycarbonyl)phenyl]-3-phenyl-1-(tetrahydro-2H-pyran-2-yl)-1H-pyrazolo[3,4-b]pyridine-4-carboxylic acid (2.0 g/4.20 mmol) in 35 mL of DCM. The solution is stirred at ambient temperature for 15 minutes and then run into water and extracted with EtOAc. The organic phase is washed with water and then with a saturated aqueous solution of NaCl, dried over sodium sulphate and concentrated to dryness to give 1.4 g of a pale yellow powder (yield: 86%).

LCMS (method 2): $[M+H]^+$=392.3, RT=13.6 min

Step 1.10. methyl 2-fluoro-5-{4-[(15-{6-[4-fluoro-3-(methoxycarbonyl)phenyl]-3-phenyl-1H-pyrazolo[3,4-b]pyridin-4-yl}-15-oxo-4,7,10-trioxa-14-azapentadec-1-yl)carbamoyl]-3-phenyl-1H-pyrazolo[3,4-b]pyridin-6-yl}benzoate PyBop® (0.59 g/1.13 mmol) is added to a solution of 6-[4-fluoro-3-(methoxycarbonyl)phenyl]-3-phenyl-1H-pyrazolo[3,4-b]pyridine-4-carboxylic acid (370 mg/0.95 mmol) and triethylamine (0.33 mL/2.36 mmol) in 4.3 mL of anhydrous THF at 0° C. under argon. After stirring at 0° C. for 30 minutes, 3,3'-[oxybis(ethane-2,1-diyloxy)]dipropan-1-amine (0.10 mL/0.47 mmol) is added. The solution is stirred at ambient temperature for 1 h and then run into a solution of KHSO$_4$ (1 M) and extracted with EtOAc. The organic phase is washed with water and with a saturated aqueous solution of NaCl, dried over sodium sulphate and concentrated to dryness to give a white powder which is used in the following step.
LCMS (method 3): [M+H]$^+$=967.2, RT=8.70 min Step 1.11. 5-[4-({15-[6-(3-carboxy-4-fluorophenyl)-3-phenyl-1H-pyrazolo[3,4-b]pyridin-4-yl]-15-oxo-4,7,10-trioxa-14-azapentadec-1-yl}carbamoyl)-3-phenyl-1H-pyrazolo[3,4-b]pyridin-6-yl]-2-fluorobenzoic acid Sodium hydroxide (1 M, 1.46 mL/1.46 mmol) is added to a suspension of methyl 2-fluoro-5-{4-[(15-{6-[4-fluoro-3-(methoxycarbonyl)phenyl]-3-phenyl-1H-pyrazolo[3,4-b]pyridin-4-yl}-15-oxo-4,7,10-trioxa-14-azapentadec-1-yl)carbamoyl]-3-phenyl-1H-pyrazolo[3,4-b]pyridin-6-yl}benzoate (370 mg/0.42 mmol) in 4 mL of DCM/MeOH (50/50). The solution is stirred at ambient temperature for 1 hour and then run into a solution of KHSO$_4$ (1 M) and extracted with EtOAc. The organic phase is washed with water and with a saturated aqueous solution of NaCl, dried over sodium sulphate and concentrated to dryness. After purification by flash chromatography on silica (DCM/EtOH 0.1% TEA: 99/1 to 80/20), the solid obtained is dissolved in MeOH and run into a solution of KHSO$_4$ (1 M). The precipitate is filtered off, washed with water and dried under vacuum to give a white powder (yield: 40% four Steps 1.7 and 1.8).
LCMS (method 3): [M+H]$^+$=939.2, RT=5.97 min Step 1.12. Lysine Salt of 5-[4-({15-[6-(3-carboxy-4-fluorophenyl)-3-phenyl-1H-pyrazolo[3,4-b]pyridin-4-yl]-15-oxo-4,7,10-trioxa-14-azapentadec-1-yl}carbamoyl)-3-phenyl-1H-pyrazolo[3,4-b]pyridin-6-yl]-2-fluorobenzoic acid 5-[4-({15-[6-(3-Carboxy-4-fluorophenyl)-3-phenyl-1H-pyrazolo[3,4-b]pyridin-4-yl]-15-oxo-4,7,10-trioxa-14-azapentadec-1-yl}carbamoyl)-3-phenyl-1H-pyrazolo[3,4-b]pyridin-6-yl]-2-fluorobenzoic acid (18.8 mg; 0.02 mmol) is added to a solution of lysine (5.8 mg; 0.04 mmol) in 1 mL of water. The solution is stirred for 1 h, filtered and lyophilized. The lyophilisate is taken up in diethyl ether and the suspension is stirred for 3 h, filtered and dried under vacuum to give 23 mg (2 lysine; 93%) of a white powder.
LCMS (method 3): [M+H]$^+$=939.2, RT=5.96 min
$^1$H NMR [(CD$_3$)$_2$SO, 250 MHz]: δ ppm 8.67 (t, 2H) 8.47 (dd, 2H) 8.06-8.15 (m, 2H) 7.70 (s, 2H) 7.55-7.60 (m, 4H) 7.51-9.53 (br. s., 8H) 7.35-7.45 (m, 6H) 7.18 (t, 2H) 3.44-3.49 (m, 4H) 3.38-3.42 (m, 4H) 3.32 (t, 4H) 3.25 (t, 2H) 3.10 (q, 4H) 2.76 (t, 4H) 1.31-1.81 (m, 16H)

EXAMPLE 2

Lysine Salt of 5-[4-({16-[6-(3-carboxy-4-fluorophenyl)-3-phenyl-1H-pyrazolo[3,4-b]pyridin-4-yl]-16-oxo-3,6,9,12-tetraoxa-15-azahexadec-1-yl}carbamoyl)-3-phenyl-1H-pyrazolo[3,4-b]pyridin-6-yl]-2-fluorobenzoic acid (Compound No. 3)

Step 2.1 methyl 2-fluoro-5-{4-[(16-{6-[4-fluoro-3-(methoxycarbonyl)phenyl]-3-phenyl-1H-pyrazolo[3,4-b]pyridin-4-yl}-16-oxo-3,6,9,12-tetraoxa-15-azahexadec-1-yl)carbamoyl]-3-phenyl-1H-pyrazolo[3,4-b]pyridin-6-yl}benzoate Obtained according to the process described in Step 1.10, using 6-[4-fluoro-3-(methoxycarbonyl)phenyl]-3-phenyl-1H-pyrazolo[3,4-b]pyridine-4-carboxylic acid [described in Step 1.9.] and 3,6,9,12-tetraoxatetradecane-1,14-diamine, in the form of a white powder (yield: 66%).
LCMS (method 4): [M+H]$^+$=983.3, RT=17.81 min Step 2.2 5-[4-({16-[6-(3-carboxy-4-fluorophenyl)-3-phenyl-1H-pyrazolo[3,4-b]pyridin-4-yl]-16-oxo-3,6,9,12-tetraoxa-15-azahexadec-1-yl}carbamoyl)-3-phenyl-1H-pyrazolo[3,4-b]pyridin-6-yl]-2-fluorobenzoic acid Obtained according to the process described in Step 1.11, using methyl 2-fluoro-5-{4-[(16-{6-[4-fluoro-3-(methoxycarbonyl)phenyl]-3-phenyl-1H-pyrazolo[3,4-b]pyridin-4-yl}-16-oxo-3,6,9,12-tetraoxa-15-azahexadec-1-yl)carbamoyl]-3-phenyl-1H-pyrazolo[3,4-b]pyridin-6-yl}benzoate, in the form of a white powder (yield: 81%).
LCMS (method 3): [M+H]$^+$=955.2, RT=10.17 min Step 2.3 Lysine Salt of 5-[4-({16-[6-(3-carboxy-4-fluorophenyl)-3-phenyl-1H-pyrazolo[3,4-b]pyridin-4-yl]-16-oxo-3,6,9,12-tetraoxa-15-azahexadec-1-yl}carbamoyl)-3-phenyl-1H-pyrazolo[3,4-b]pyridin-6-yl]-2-fluorobenzoic acid Obtained according to the process described in Step 1.12, using 5-[4-({16-[6-(3-carboxy-4-fluorophenyl)-3-phenyl-1H-pyrazolo[3,4-b]pyridin-4-yl]-16-oxo-3,6,9,12-tetraoxa-15-azahexadec-1-yl}carbamoyl)-3-phenyl-1H-pyrazolo[3,4-b]pyridin-6-yl]-2-fluorobenzoic acid, in the form of a white powder (yield: 91%).
LCMS (method 4): [M+H]$^+$=955.2, RT=10.27 min
$^1$H NMR (500 MHz, DMSO-d$_6$) δ ppm 8.82 (t, 2H) 8.46 (dd, 2H) 8.07-8.13 (m, 2H) 7.70 (s, 2H) 7.55-7.61 (m, 4H) 7.35-7.46 (m, 6H) 7.19 (t, 2H) 3.44 (d, 12H) 3.34 (t, 4H) 3.21 (dt, 6H) 2.75 (t, 4H) 1.58-1.78 (m, 4H) 1.32-1.57 (m, 8H)

EXAMPLE 3

Lysine Salt of 5-(4-carbamoyl-3-{3-[(15-{3-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid (Compound No. 6)

Step 3.1 3-{3-[(benzyloxy)carbonyl]phenyl}-6-[4-fluoro-3-(methoxycarbonyl)phenyl]-1-(tetrahydro-2H-pyran-2-yl)-1H-pyrazolo[3,4-b]pyridine-4-carboxylic acid The ligand sodium 2'-dicyclohexylphosphino-2,6-dimethoxy-1,1'-biphenyl-3-sulphonate hydrate (146 mg/0.3 mmol) and the catalyst PdCl$_2$(dppf) (280 mg/0.36 mmol) are added successively, under argon, to a suspension of 6-[4-fluoro-3-(methoxycarbonyl)phenyl]-3-iodo-1-(tetrahydro-2H-pyran-2-yl)-1H-pyrazolo[3,4-b]pyridine-4-carboxylic acid [described in Step 1.7.] (1.5 g/3 mmol), benzyl 3-(4,4,5,5-tetramethyl-1,3,2-dioxaborolan-2-yl)benzoate [880157-10-8] (1.16 g/3.4 mmol) and potassium carbonate (828 mg/6.0 mmol) in 9.5 mL of DMF. The reaction mixture is heated at 95° C. for 1 h. It is run into a saturated aqueous solution of NaHCO$_3$ and extracted with EtOAc. The organic phase is washed with water and with a saturated aqueous solution of NaCl, dried over sodium sulphate, filtered and concentrated to dryness. After purification by flash chromatography on silica (DCM/EtOH 0.1% TEA: 100/0 to 90/10), 1.31 g of a yellow solid are obtained (triethylamine salt; yield: 72%).

LCMS (method 1): [M+H]$^+$=610.2, RT=10.38 min

Step 3.2 methyl 5-[3-{3-[(benzyloxy)carbonyl]phenyl}-4-carbamoyl-1-(tetrahydro-2H-pyran-2-yl)-1H-pyrazolo[3,4-b]pyridin-6-yl]-2-fluorobenzoate Triethylamine (0.57 mL/4.0 mmol), PyBop® (1.26 g/2.4 mmol) and ammonium hydrogen carbonate (192 mg/2.4 mmol) are successively added to a suspension of 3-{3-[(benzyloxy)carbonyl]phenyl}-6-[4-fluoro-3-(methoxycarbonyl)phenyl]-1-(tetrahydro-2H-pyran-2-yl)-1H-pyrazolo[3,4-b]pyridine-4-carboxylic acid (1.2 g/2.0 mmol) in 10 mL of anhydrous MeTHF under nitrogen. The mixture is stirred at ambient temperature for 2 hours and then run into a saturated aqueous solution of NaHCO$_3$ and extracted with EtOAc. The organic phase is washed with water and with a saturated aqueous solution of NaCl, dried over sodium sulphate, filtered, concentrated to dryness and oven-dried under vacuum to give 1.02 g of a beige powder (yield: 84%).

LCMS (method 1): [M+H]$^+$=609.2, RT=9.89 min

Step 3.3 3-{4-carbamoyl-6-[4-fluoro-3-(methoxycarbonyl)phenyl]-1H-pyrazolo[3,4-b]pyridin-3-yl}benzoic acid Methyl 5-[3-{3-[(benzyloxy)carbonyl]phenyl}-4-carbamoyl-1-(tetrahydro-2H-pyran-2-yl)-1H-pyrazolo[3,4-b]pyridin-6-yl]-2-fluorobenzoate (1.0 g/1.64 mmol) is dissolved in 6.8 mL of concentrated sulphuric acid. The solution is stirred at ambient temperature for 30 min and then run into ice-cold water and stirred for 30 min. The precipitate obtained is filtered off, washed with water and dissolved in EtOAc/MeTHF (50/50). The solution is washed with water and with a saturated aqueous solution of NaCl, dried over sodium sulphate, filtered and concentrated to dryness. The solid is taken up with a mixture of DCM/methanol, filtered and dried under vacuum to give 0.85 g of a beige powder (yield: 85%).

LCMS (method 1): [M+H]$^+$=435.0, RT=6.43 min

Step 3.4 methyl 5-[4-carbamoyl-3-(3-{([15-(3-{4-carbamoyl-6-[4-fluoro-3-(methoxycarbonyl)phenyl]-1H-pyrazolo[3,4-b]pyridin-3-yl}phenyl)-15-oxo-4,7,10-trioxa-14-azapentadec-1-yl]carbamoyl}phenyl)-1H-pyrazolo[3,4-b]pyridin-6-yl]-2-fluorobenzoate Obtained according to the process described in Step 1.10, using 3-{4-carbamoyl-6-[4-fluoro-3-(methoxycarbonyl)phenyl]-1H-pyrazolo[3,4-b]pyridin-3-yl}benzoic acid and 3,3'-[oxybis(ethane-2,1-diyloxy)]dipropan-1-amine. The reaction medium is directly run into a solution of KHSO$_4$ (1 M) to give, after filtration, washing with water and with diisopropylethyl ether and then drying, a white powder (yield: 66%).

LCMS (method 3): [M+H]$^+$=1053.2, RT=7.49 min

Step 3.5 5-(4-carbamoyl-3-{3-[(15-{3-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid Obtained according to the process described in Step 1.11, using methyl 5-[4-carbamoyl-3-(3-{[15-(3-{4-carbamoyl-6-[4-fluoro-3-(methoxycarbonyl)phenyl]-1H-pyrazolo[3,4-b]pyridin-3-yl}phenyl)-15-oxo-4,7,10-trioxa-14-azapentadec-1-yl]carbamoyl}phenyl)-1H-pyrazolo[3,4-b]pyridin-6-yl]-2-fluorobenzoate, in the form of a white powder (yield: 60%).

LCMS (method 6): [M+H]$^+$=1025.5, RT=1.78 min

Step 3.6 Lysine Salt of 5-(4-carbamoyl-3-{3-[(15-{3-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid Obtained according to the process described in Step 1.12, using 5-(4-carbamoyl-3-{3-[(15-{3-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid, in the form of a white powder (yield: 64%).

LCMS (method 3): [M+H]$^+$=1025.3, RT=5.17 min $^1$H NMR (500 MHz, DMSO-d$_6$): 6 ppm 8.52 (dd, 2H), 8.42 (t, 2H), 8.20 (s, 2H), 8.11-8.18 (m, 4H), 7.85 (dt, 2H), 7.78 (s, 2H), 7.71-7.76 (m, 4H), 7.50 (t, 2H), 7.23 (t, 2H), 3.45-3.53 (m, 12H), 3.34 (q, 4H), 3.22 (t, 1H), 2.77 (t, 2H), 1.78 (quin, 4H), 1.33-1.74 (m, 6H)

EXAMPLE 4

Lysine Salt of 5-(4-carbamoyl-3-{4-[(15-{4-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid (Compound No. 8)

Step 4.1 3-{4-[(benzyloxy)carbonyl]phenyl}-6-[4-fluoro-3-(methoxycarbonyl)phenyl]-1-(tetrahydro-2H-pyran-2-yl)-1H-pyrazolo[3,4-b]pyridine-4-carboxylic acid Obtained according to the process described in Step 3.1, using benzyl 4-(4,4,5,5-tetramethyl-1,3,2-dioxaborolan-2-yl)benzoate and 6-[4-fluoro-3-(methoxycarbonyl)phenyl]-3-iodo-1-(tetrahydro-2H-pyran-2-yl)-1H-pyrazolo[3,4-b]pyridine-4-carboxylic acid [described in Step 1.7], in the form of a yellow solid (yield: 66%).

LCMS (method 1): [M+H]$^+$=610.2, RT=10.48 min

Step 4.2 methyl 5-[3-{4-[(benzyloxy)carbonyl]phenyl}-4-carbamoyl-1-(tetrahydro-2H-pyran-2-yl)-1H-pyrazolo[3,4-b]pyridin-6-yl]-2-fluorobenzoate Obtained according to the process described in Step 3.2, using 3-{4-[(benzyloxy)carbonyl]phenyl}-6-[4-fluoro-3-

(methoxycarbonyl)phenyl]-1-(tetrahydro-2H-pyran-2-yl)-1H-pyrazolo[3,4-b]pyridine-4-carboxylic acid, in the form of a beige solid (yield: 79%).
LCMS (method 1): [M+H]⁺=609.2, RT=9.91 min Step 4.3 4-{4-carbamoyl-6-[4-fluoro-3-(methoxycarbonyl)phenyl]-1H-pyrazolo[3,4-b]pyridin-3-yl}benzoic acid Obtained according to the process described in Step 3.3, using methyl 5-[3-{4-[(benzyloxy)carbonyl]phenyl}-4-carbamoyl-1-(tetrahydro-2H-pyran-2-yl)-1H-pyrazolo[3,4-b]pyridin-6-yl]-2-fluorobenzoate, in the form of a yellow solid (yield: 85%).
LCMS (method 1): [M−H]⁺=435.0, RT=6.48 min Step 4.4 methyl 5-[4-carbamoyl-3-(4-{[15-(4-{4-carbamoyl-6-[4-fluoro-3-(methoxycarbonyl)phenyl]-1H-pyrazolo[3,4-b]pyridin-3-yl}phenyl)-15-oxo-4,7,10-trioxa-14-azapentadec-1-yl]carbamoyl}phenyl)-1H-pyrazolo[3,4-b]pyridin-6-yl]-2-fluorobenzoate Obtained according to the process described in Step 1.10, using 4-{4-carbamoyl-6-[4-fluoro-3-(methoxycarbonyl)phenyl]-1H-pyrazolo[3,4-b]pyridin-3-yl}benzoic acid and 3,3'-[oxybis(ethane-2,1-diyloxy)]dipropan-1-amine, in the form of a white powder (yield: 55%).
LCMS (method 3): [M−H]⁺=1053.2, RT=7.29 min Step 4.5 5-(4-carbamoyl-3-{4-[(15-{4-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid Obtained according to the process described in Step 1.11, using methyl 5-[4-carbamoyl-3-(4-{[15-(4-{4-carbamoyl-6-[4-fluoro-3-(methoxycarbonyl)phenyl]-1H-pyrazolo[3,4-b]pyridin-3-yl}phenyl)-15-oxo-4,7,10-trioxa-14-azapentadec-1-yl]carbamoyl}phenyl)-1H-pyrazolo[3,4-b]pyridin-6-yl]-2-fluorobenzoate, in the form of a white powder (yield: 62%).
LCMS (method 3): [M+H]⁺=1025.3, RT=5.19 min Step 4.6 Lysine Salt of 5-(4-carbamoyl-3-{4-[(15-{4-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid (Compound No. 8)

Obtained according to the process described in Step 1.11, using 5-(4-carbamoyl-3-{4-[(15-{4-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid, in the form of a white powder (yield: 78%).
LCMS (method 4): [M+H]⁺=1025.3, RT=8.48 min
¹H NMR (500 MHz, DMSO-d₆): δ ppm 8.49 (dd, 2H) 8.43 (t, 2H) 8.23 (s, 2H) 8.14-8.18 (m, 2H) 8.07-8.12 (m, 2H) 7.82-7.87 (m, 2H) 7.76 (s, 2H) 7.70-7.75 (m, 4H) 7.49 (t, 2H) 7.19 (t, 2H) 7.03 (br. s., 10H) 3.50-3.85 (br. s, 4H) 3.43-3.55 (m, 12H) 3.34 (dd, 4H) 3.20 (t, 2H) 2.73 (t, 4H) 1.78 (quin, 4H) 1.32-1.73 (m, 12H)

The table which follows illustrates the chemical structures and the physical properties of some examples of compounds according to the invention. In this table, in the "salt" column, "Lys" represents a compound in D,L-lysine salt form, and the ratio between parentheses is the (base:diacid) ratio.

TABLE OF EXAMPLES

M₁-L-M₂ with M having the general formula as below:

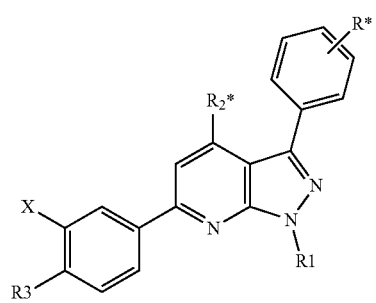

| No. | R | R1 | R2 | R3 | X | L | Salt | [M + H]⁺ | RT (min) | LCMS Method |
|---|---|---|---|---|---|---|---|---|---|---|
| 1 | H | H | —CONH* | —CO₂H | F | *(CH₂)₃O(CH₂)₂O(CH₂)₃* | Lys (2) | 895 | 1.12 | 7 |
| 2 | H | H | —CONH* | —CO₂H | F | *(CH₂)₃[O(CH₂)₂]₂O(CH₂)₃* | Lys (2) | 939 | 5.96 | 3 |
| 3 | H | H | —CONH* | —CO₂H | F | *(CH₂)₂[O(CH₂)₂]₃O(CH₂)₂* | Lys (2) | 955 | 10.27 | 4 |
| 4 | H | H | —CONH* | —CO₂H | F | *(CH₂)₂[O(CH₂)₂]₄O(CH₂)₂* | Lys (2) | 999 | 1.11 | 7 |
| 5 | H | H | —CONH* | —CO₂H | F | *(CH₂)₃[O(CH₂)₂]₄O(CH₂)₃* | Lys (2) | 1027 | 3.80 | 8 |
| 6 | meta-CONH* | H | —CONH₂ | —CO₂H | F | *(CH₂)₃[O(CH₂)₂]₂O(CH₂)₃* | Lys (2) | 1025 | 5.17 | 3 |
| 7 | meta-CONH* | H | —CONH₂ | —CO₂H | F | *(CH₂)₂O(CH₂)₂O(CH₂)₂* | Lys (2) | 953 | 4.76 | 3 |
| 8 | para-CONH* | H | —CONH₂ | —CO₂H | F | *(CH₂)₃[O(CH₂)₂]₂O(CH₂)₃* | Lys (2) | 1025 | 8.48 | 4 |
| 9 | para-CONH* | H | —CONH₂ | —CO₂H | F | *(CH₂)₂O(CH₂)₂O(CH₂)₂* | Lys (2) | 953 | 7.33 | 3 |

The results of pharmacological tests in vitro and in vivo carried out with a view to determining properties of the compounds of the invention are listed below;

| Compound | % activation with respect to FGF2 (in vitro) | EC50 |
|---|---|---|
| 1 | 84% | EC50 <1 nM |
| 2 | 84% | EC50 <1 nM |
| 3 | 75% | EC50 <1 nM |
| 5 | 124% | EC50 <1 nM |
| 6 | 50% | EC50 = 3 nM |
| 8 | 20% | EC50 <100 nM |
| 9 | 60% | EC50 <1 nM |

In Vitro Angiogenesis Model

The products are tested for their ability to cause rearrangement of human venous endothelial cells (HUVECs) on matrigel (Becton dickinson 356230) diluted in collagen (rat tail collagen, type I: Becton dickinson 354236). After 24 hours, the cells are observed under a microscope with a X4 objective and the length of the pseudotubules is measured by means of an image analyser (BIOCOM-logiciel Visiolab 2000).

For the in vitro angiogenesis test, the compounds of the invention demonstrated a specific activity of between $10^{-6}$ M and $10^{-12}$ M. By way of example, compounds 1, 2, 3, 5 and 9 are active at a concentration of 1 nM on the in vitro angiogenesis model.

Sponge Angiogenesis Model

The sponge angiogenesis model is an adaptation of the technique of Andrade et al [Andrade S P, Machado R., Teixeir A S, Belo A V, Tarso A M, Beraldo W T—Sponge-induced angiogenesis in mice and the pharmacological reactivity of the neovasculature quantitated by fluorimetric method, Microvascular Research, 1997, 54: 253-61.]

The mice used are BalbC females from Charles River Laboratory, 7 to 10 weeks old. The animals are anaesthetized by intraperitoneal injection of a xylazine/ketamine mixture (1 mg/kg each in 0.9% NaCl). The animal's back is shaved and disinfected with hexomedine. A subcutaneous 5 ml pocket of air is made on the animal's back with sterile air. An incision is then made (approximately 1 cm) on the top of the animal's back in order to implant the sponge into the pocket. The biocompatible cellulose sponge (Cellspon, Interchim, 10 mm in diameter) was sterilized beforehand (autoclave 20 min at 120° C.) and is impregnated with 50 µl of sterile solution containing the test product. Suturing is performed by inserting two 9-mm stainless steel autoclip staples (Subra). The wound is again disinfected with hexomedine. The animals are housed in individual cages throughout the duration of the experiment.

The test products are in solution in a PBS/0.1% BSA mixture: the recombinant human FGF2 (Peprotech) and the products of the invention are placed in solution extemporaneously according to the concentration selected. On the two days following the implantation of the cellulose sponge, the test products in solution are reinjected directly into the implant through the animal's skin, after having disinfected the area with hexomedine.

On the eighth day after implantation, the mice are sacrificed with a lethal dose of sodium pentobarbital (CEVA santé animale, 10 mg/kg) administered intraperitoneally. The skin is cut out around the sponge (approximately 1 cm) and the sponge is separated from the skin by removing the connective tissue. The sponge is cut into 3 or 4 pieces and placed in a tube containing ceramic beads with 1 mL of RIPA lysis buffer. The lysis is performed by means of two cycles of agitation for 20 seconds (FastPrep® FP 120). After freezing of the supernatants at −20° C., the tubes are centrifuged at 8000 rpm for 10 minutes and the supernatants are removed in order to assay the haemoglobin.

To assay the haemoglobin, 50 µl of each sample are deposited in a 96-well plate, in duplicate. The range is prepared with human haemoglobin (ref H7379, Sigma®) in a solution of 4 mg/ml to 0.06 mg/ml in the RIPA lysis buffer. 50 µl of Drabkin reagent (Sigma®) are deposited in all the wells (range+samples). The plate is incubated for 15 min at ambient temperature, in the dark. The OD values are read on a spectrophotometer at 405 nm, using the Biolise software (Tecan, France). The Hb concentration in each sample is expressed in mg/mL according to the polynomial regression performed using the range.

By way of example, compound 2 is active at a concentration of 300 µM injected into the sponge on the in vivo angiogenesis model.

The compounds of the invention exhibit an FGF receptor agonist activity. They induce receptor dimerization and, by virtue of their low toxicity and their pharmacological and biological properties, the compounds of the present invention represent a therapy of choice in pathological conditions for which FGFs have a positive effect, such as post-ischaemic revascularization, healing processes, and neuronal, muscle and bone repair and regeneration processes.

One of the applications of the compounds of the invention is treatment requiring an increase in angiogenesis, such as post-ischaemic treatment after occlusion of peripheral arteries or treatment of the consequences of cardiac ischaemia. The compounds described in the invention can be of use in the treatment of diseases associated with narrowing or obstruction of coronary arteries or of arteritis, and in particular in the treatment of angina pectoris or of thromboangiitis obliterans. Moreover, the compounds of said invention could represent a treatment of choice for compensating for a deficiency in angiogenesis in pre-eclamptic placentas. Through their anti-apoptotic activity on endothelial cells, the products of said invention could provide a treatment choice in vascular improvement in patients suffering from vascular damage, and in particular patients suffering from ARDS.

Through their FGF receptor agonist activities and their abilities to induce angiogenesis and to activate mesenchymal cells involved in the phases of healing, the compounds of said invention would represent a therapy of choice for treating healing, in particular in elderly or diabetic patients. The compounds presented in the invention could represent a treatment of choice for muscle regeneration.

By virtue of the FGF receptor agonist activity, the compounds of said invention would represent a treatment of choice in the treatment of nociception, in the treatment of chronic pain and in the treatment of peripheral neuropathy, in particular in diabetic patients.

Through the FGF receptor agonist properties, the compounds of said invention could represent a treatment of choice in bone repair after fracture.

Through their FGF receptor agonist activity, the compounds of said invention could provide a treatment of choice for hair-follicle repair and protection and in the protection and regulation of hair growth.

A subject of the present invention, according to another of its aspects, is therefore the use of a compound as defined above, for preparing a medicament that is of use in the treatment of diseases requiring FGF receptor activation.

A subject of the present invention is more particularly the use of a compound as defined above, for preparing a medicament that is of use in the treatment of cardiac ischaemia, the treatment of diseases associated with narrowing or obstruction of the arteries or of arteritis, the treatment of angina pectoris, the treatment of thromboangiitis obliterans, the treatment of atherosclerosis, treatment for inhibiting post-angioplasty or post-endoarterectomy restenosis, the treatment of healing, treatment for muscle regeneration, treatment for myoblast survival, treatment for sarcopenia, loss of functionality of the smooth muscles of the sphincters, the treatment of nociception and the treatment of chronic pain, the treatment of peripheral neuropathy, treatment for improving bioartificial pancreatic graft survival in diabetic patients, treatment to bring about a decrease in cholesterol associated with a decrease in adiposity, treatment for improving graft revascularization and graft survival, the treatment of retinal degeneration, the treatment of pigmentary retinitis, the treatment of osteoarthritis, the treatment of pre-eclampsia, the treatment of vascular lesions and of acute respiratory distress syndrome, bone protection treatment, or treatment for hair-follicle protection.

According to another aspect, the compounds of the invention are of use for the treatment of cardiac ischaemia, the treatment of diseases associated with narrowing or obstruction of the arteries or of arteritis, the treatment of angina pectoris, the treatment of thromboangiitis obliterans, the treatment of atherosclerosis, treatment for inhibiting post-angioplasty or post-endoarterectomy restenosis, the treatment of healing, treatment for muscle regeneration, treatment for myoblast survival, treatment for sarcopenia, loss of functionality of the smooth muscles of the sphincters, the treatment of nociception and the treatment of chronic pain, the treatment of peripheral neuropathy, treatment for improving bioartificial pancreatic graft survival in diabetic patients, treatment to bring about a decrease in cholesterol associated with a decrease in adiposity, treatment for improving graft revascularization and graft survival, the treatment of retinal degeneration, the treatment of the pigmentary retinitis, the treatment of osteoarthritis, the treatment of pre-eclampsia, the treatment of vascular lesions and of acute respiratory distress syndrome, bone protection treatment, or treatment for hair-follicle protection.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, and also at least one pharmaceutically acceptable excipient.

Said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, can be administered in unit administration form, as a mixture with conventional pharmaceutical excipients, to animals or to human beings for the prophylaxis or treatment of the above disorders or diseases.

The appropriate unit administration forms include oral forms, such as tablets, soft or hard gel capsules, powders, granules and oral solutions or suspensions, sublingual, buccal, intratracheal, intraocular and intranasal administration forms, forms of administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following constituents:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating and/or preventing the pathological conditions indicated above, which comprises the administration, to a patient, of an effective dose of a compound according to the invention, or a pharmaceutically acceptable salt thereof.

The invention claimed is:

1. FGF receptor agonist compounds corresponding to the general formula:

$$M_1\text{-}L\text{-}M_2$$

in which $M_1$ and $M_2$, which may be identical or different, each represent, independently of one another, a monomer unit M and L represents a linker group which links $M_1$ and $M_2$ covalently, characterized in that said monomer unit corresponds to the general formula M which follows:

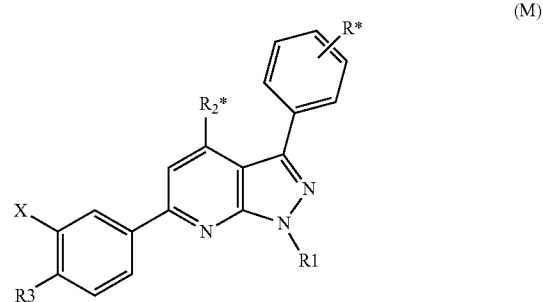

(M)

in which:
the asterisk * indicates the site of linkage between the monomer and the linker L, said linkage site of each monomer unit $M_1$ and $M_2$ being located on one of the substituents R or $R_2$,
R represents a hydrogen atom (in which case the site of linkage of L with M is located on $R_2$) or a group —CONH*,
$R_1$ represents a hydrogen atom or a linear ($C_1$-$C_3$)alkyl group,
$R_2$ represents a group —$CONH_2$ (in which case the site of linkage of L with M is located on R) or —CONH*,
$R_3$ represents a group —$CO_2R_4$, where $R_4$ represents a hydrogen atom or a linear ($C_1$-$C_4$)alkyl group, and X is a halogen atom chosen from fluorine, chlorine and bromine atoms, in the form of a base or of an addition salt with an acid or with a base.

2. FGF receptor agonist compounds according to claim 1, characterized in that $R_1$ represents a hydrogen atom, in the form of a base or of an addition salt with an acid or with a base.

3. FGF receptor agonist compounds according to claim 1, characterized in that $R_3$ represents a group —$CO_2R_4$, with $R_4$ representing a hydrogen atom, in the form of a base or of an addition salt with an acid or with a base.

4. FGF receptor agonist compounds according to claim 1, characterized in that X represents a fluorine atom, in the form of a base or of an addition salt with an acid or with a base.

5. FGF receptor agonist compounds according to claim 1, characterized in that:

R represents a group —CONH*, where the asterisk * indicates the site of linkage of L, firstly, with the monomer unit $M_1$ and, secondly, with the monomer unit $M_2$, $R_1$ represents a hydrogen atom or a linear ($C_1$-$C_3$)alkyl group and advantageously a hydrogen atom, in the form of a base or of an addition salt with an acid or with a base.

6. FGF receptor agonist compounds according to claim 1, characterized in that R is located in the meta or para position, in the form of a base or of an addition salt with an acid or with a base.

7. FGF receptor agonist compounds according to claim 1, characterized in that:

R represents a hydrogen atom, $R_2$ represents a group —CONH*, where the asterisk * indicates the site of linkage of L, firstly, with the monomer unit $M_1$ and, secondly, with the monomer unit $M_2$, in the form of a base or of an addition salt with an acid or with a base.

8. FGF receptor agonist compounds according to claim 1, characterized in that the linker group L can be more particularly chosen from the following PEG radicals:

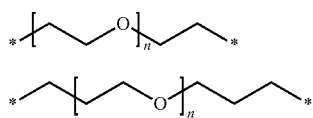

(A)

(B)

in which the asterisk * indicates the atom for linkage of L with the monomer unit M on the substituent R* or $R_2$*;

n represents an integer from 2 to 6, in the form of a base or of an addition salt with an acid or with a base.

9. FGF receptor agonist compounds according to claim 1, characterized in that n is an integer of 3 or 4, in the form of a base or of an addition salt with an acid or with a base.

10. Compound according to claim 1, characterized in that it is chosen from:

Compound No. 1: 3,3'-{ethane-1,2-diylbis[oxypropane-3,1-diylcarbamoyl(3-phenyl-1H-pyrazolo[3,4-b]pyridine-4,6-diyl)]}bis(6-fluorobenzoic acid);

Compound No. 2: 5-[4-({15-[6-(3-carboxy-4-fluorophenyl)-3-phenyl-1H-pyrazolo[3,4-b]pyridin-4-yl]-15-oxo-4,7,10-trioxa-14-azapentadec-1-yl}carbamoyl)-3-phenyl-1H-pyrazolo[3,4-b]pyridin-6-yl]-2-fluorobenzoic acid;

Compound No. 3: 5-[4-({16-[6-(3-carboxy-4-fluorophenyl)-3-phenyl-1H-pyrazolo[3,4-b]pyridin-4-yl]-16-oxo-3,6,9,12-tetraoxa-15-azahexadec-1-yl}carbamoyl)-3-phenyl-1H-pyrazolo[3,4-b]pyridin-6-yl]-2-fluorobenzoic acid;

Compound No. 4: 5-[4-({19-[6-(3-carboxy-4-fluorophenyl)-3-phenyl-1H-pyrazolo[3,4-b]pyridin-4-yl]-19-oxo-3,6,9,12,15-pentaoxa-18-azanonadec-1-yl}carbamoyl)-3-phenyl-1H-pyrazolo[3,4-b]pyridin-6-yl]-2-fluorobenzoic acid;

Compound No. 5: 5-[4-({21-[6-(3-carboxy-4-fluorophenyl)-3-phenyl-1H-pyrazolo[3,4-b]pyridin-4-yl]-21-oxo-4,7,10,13,16-pentaoxa-20-azahenicos-1-yl}carbamoyl)-3-phenyl-1H-pyrazolo[3,4-b]pyridin-6-yl]-2-fluorobenzoic acid;

Compound No. 6: 5-(4-carbamoyl-3-{3-[(15-{3-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid;

Compound No. 7: 3,3'-{ethane-1,2-diylbis[oxyethane-2,1-diylcarbamoylbenzene-3,1-diyl(4-carbamoyl-1H-pyrazolo[3,4-b]pyridine-3,6-diyl)]}bis(6-fluorobenzoic acid);

Compound No. 8: 5-(4-carbamoyl-3-{4-[(15-{4-[4-carbamoyl-6-(3-carboxy-4-fluorophenyl)-1H-pyrazolo[3,4-b]pyridin-3-yl]phenyl}-15-oxo-4,7,10-trioxa-14-azapentadec-1-yl)carbamoyl]phenyl}-1H-pyrazolo[3,4-b]pyridin-6-yl)-2-fluorobenzoic acid; and Compound No. 9: 3,3'-{ethane-1,2-diylbis[oxyethane-2,1-diylcarbamoylbenzene-4,1-diyl(4-carbamoyl-1H-pyrazolo[3,4-b]pyridine-3,6-diyl)]}bis(6-fluorobenzoic acid).

11. Process for preparing an FGF receptor agonist compound according to claim 1, comprising the reaction of at least one monomer comprising at least one carboxylic acid group with a reactant of formula $H_2N$-L-$NH_2$ after activation.

12. A pharmaceutical composition comprising an FGF receptor agonist compound according to claim 1, or an addition salt of this compound with a pharmaceutically acceptable acid or base of this compound.

13. A pharmaceutical composition comprising a compound according to claim 1, or a pharmaceutically acceptable salt of this compound, and also at least one pharmaceutically acceptable excipient.

* * * * *